United States Patent [19]

Heilman

[11] 4,452,251

[45] Jun. 5, 1984

[54] SYRINGE CONTENT INDICATING DEVICE

[75] Inventor: Marlin S. Heilman, Gibsonia, Pa.

[73] Assignee: Medrad, Inc., Pittsburgh, Pa.

[21] Appl. No.: 439,576

[22] Filed: Nov. 5, 1982

[51] Int. Cl.³ .............................................. A61B 6/00
[52] U.S. Cl. ................................... 128/655; 604/111; 116/227
[58] Field of Search ............... 128/655, 630, 654, 404; 604/111, 187, 218; 116/227

[56] References Cited

U.S. PATENT DOCUMENTS

| 182,192 | 9/1876 | Hicks et al. |
| 330,621 | 11/1885 | Reichardt |
| 1,225,604 | 5/1917 | Ernst |
| 3,156,236 | 11/1964 | Williamson |
| 3,313,291 | 4/1967 | Marshall |
| 3,623,474 | 11/1971 | Heilman |
| 3,701,345 | 10/1972 | Heilman |
| 3,812,843 | 5/1974 | Wootten et al. |
| 3,884,228 | 5/1975 | Hahn |
| 3,890,968 | 6/1975 | Pierce et al. |
| 3,898,637 | 8/1975 | Wolstenholme |
| 3,901,231 | 8/1975 | Olson |
| 4,001,801 | 1/1977 | Moulet |
| 4,006,736 | 2/1977 | Kranys et al. |

Primary Examiner—John D. Yasko
Attorney, Agent, or Firm—Fleit, Jacobson, Cohn & Price

[57] ABSTRACT

A means for detecting the presence of a transparent liquid in the barrel of a transparent angiography syringe comprising at least one indicator pattern positioned on the exterior of the barrel, the indicator pattern being a discrete, opaque pattern. When the syringe is empty, the indicator pattern is seen as having a first elliptical configuration; however, when the fluid is present in the barrel, the indicator pattern appears to have a second circular configuration, and the difference in apparent configuration is indicative of the presence of the liquid.

8 Claims, 3 Drawing Figures

SYRINGE CONTENT INDICATING DEVICE

BACKGROUND OF THE INVENTION

1. Field of the Invention

The present invention relates to means for determining the presence of a transparent liquid in a transparent angiographic syringe barrel and, more particularly, to means by which the presence of such a liquid is indicated by an alteration in the shape of an indicator pattern when viewed through the barrel.

2. Description of the Prior Art

One of the dangers involved in the injection of fluids into a patient is the risk that air will be accidentally injected into the patient. This danger is particularly acute in the case of angiographic equipment where blood vessels are sludied by using x-rays while injecting a contrast medium into the body through a catheter inserted in a blood vessel. The contrast medium is frequently colorless, and because such procedures are usually performed under relatively low light levels to facilitate reading of the x-rays, the ever-present danger is magnified. It is therefore highly desirable to provide a means whereby the presence of an empty or an only partially filled syringe can be readily detected prior to the attempted injection.

One approach to the problem of fluid presence detection is set forth in U.S. Pat. No. 4,006,736, issued on Feb. 8, 1977, to Kranys et al. That patent describes two different circuits for detecting the presence of air in a syringe cartridge by monitoring motor current or utilizing a characteristic of the syringe-fluid combination. Such systems are quite complicated and expensive.

U.S. Pat. No. 330,621, issued on Nov. 17, 1885, to Reichardt, shows, in a hypodermic syringe, a glass tube in which graduation lines on the back of the tube are magnified when viewed through a liquid to faciitate reading. In the absence of the liquid, the graduations are not magnified and do not appear as though extending entirely around the transparent tube. In this way the magnification of the graduations indicates the quantity of a liquid in the syringe.

U.S. Pat. No. 1,225,604, issued on May 8, 1917, to Ernst, relates to a sight gauge which includes a spaced member having vertical rows of circular holes which appear circular when the glass tube is empty, and appear transversely elongated when water is present in the glass.

While the foregoing prior art disclosures relating to fluid presence detection may be useful in the particular applications described therein, they are inadequate for syringes used in connection with angiographic injectors such as those described in U.S. Pat. No. 4,006,736. Such apparatus includes a syringe cartridge housed within a pressure jacket. The pressure jacket is generally of a clear polycarbohydrate material and the syringe is typically a polyethylene material which is also clear. However, in the low-light levels typically experienced during an angiographic scan, graduations and lines such a those described in the Reichardt patent are not readily distinguishable. Similarly, the circular openings described in the Ernst patent are not useful under those conditions because they depend upon the transmission of light through the back of the syringe from all directions. In contrast, angiographic injectors are typically used with the light being directed from above.

Accordingly, it is an object of the present invention to provide a means whereby the presence of an empty or an only partially filled syringe can be readily detected under lowlight levels prior to injection by direct visual means and without the use of electronic circuitry, backlighting or the like.

SUMMARY OF THE INVENTION

Briefly stated, in accordance with one aspect of the present invention, a fluid presence indicating means is provided for use with a syringe having a transparent, hollow cylindrical barrel for receiving a transparent liquid, the barrel including a plunger axially reciprocable therewithin. The indicating means is positioned in the outer surface of the barrel to indicale the presence of the transparent liquid and includes a plurality of discrete, opaque patterns of predetermined shape which are axially disposed along the barrel. When liquid is present in the barrel the perceived configuration of the patterns is altered and thereby provides a direct visual indication of the presence of a transparent liquid within the barrel.

DESCRIPTION OF THE PREFERRED EMBODIMENTS

Figure 1:
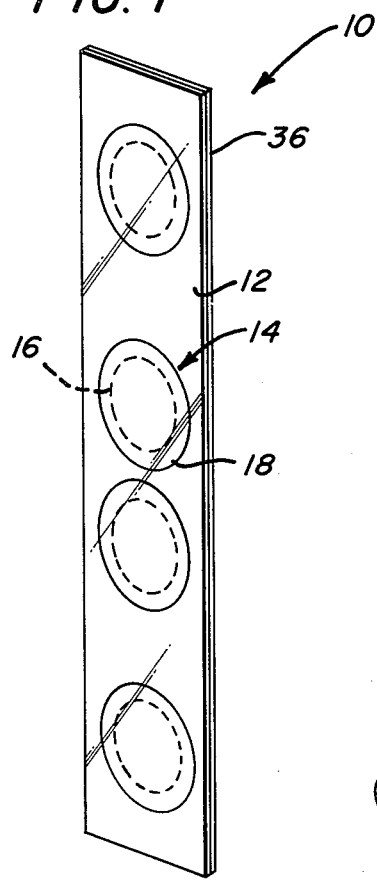
FIG. 1 is a perspective view of one embodiment of the indicating means of the present invention which can be applied to a transparent syringe barrel.

Referring now to the drawings, and particularly to FIG. 1 thereof, there is shown one embodiment of an indicating means according to the present invention wherein the means is a separate device for attachment to the outer surface of the barrel of a syringe cartridge, such as that cartridge shown in U.S. Pat. No. 4,006,736. Indicating means 10 is a strip 12 of relatively thin, transparent material having a sufficient length that it extends along a substantial portion of the axial length of the barrel. Provided on one surface of strip 12 is at least one dark indicator pattern 14 for detecting the presence or absence of liquid within the barrel, as will hereinafter be described in more detail. Indicator pattern 14 can comprise a central elliptical portion 16, as shown, with its longer axis oriented along the length of the strip. Surrounding the elliptical portion 16 can be a light border 18 to provide contrast for the dark ellipse and thereby facilitate viewing of the portion 16 in the low light levels common during angiographic injection procedures.

In a preferred arrangement, strip 12 will have more than one indicator pattern 14 along its length, the number of indicator patterns 14 depending in part on the length of the syringe with which it is used. In order to provide an effective indicator pattern 14, each ellipse can have a major axis length approximately equal to the width of the transparent strip 10, with a minor axis whose length is approximately 60% of the major axis length. At the minor axis, the darkened center portion extends over at least about one half of the axis length of the outer white ellipse.

The overall dimensions of the ellipses can be chosen so that when viewed through a full syringe, the ellipses appear generally circular. As the dimensions of the barrel and the presence or absence of fluid in the syringe affect the resulting appearance, the dimensions can be selected so that in each combination of barrel size and content the basically circular appearance results. In a preferred embodiment the strips can be used with syringe barrels of two different sizes, and in that instance the dimensions of the ellipses are usually a compromise between the ideal dimensions for each of the individual syringe barrel sizes involved.

The light and dark ellipse patterns can be printed upon the clear backing strip in any suitable manner. In the preferred embodiment, one side of the transparent strip 10 is covered first with a suitable pressure sensitive adhesive and then the latter is covered by a removable backing strip 36 (see FIG. 3). The arrangement of the indicator strip in this manner permits quick and easy installation of the strip upon existing syringe barrels.

Figure 2:
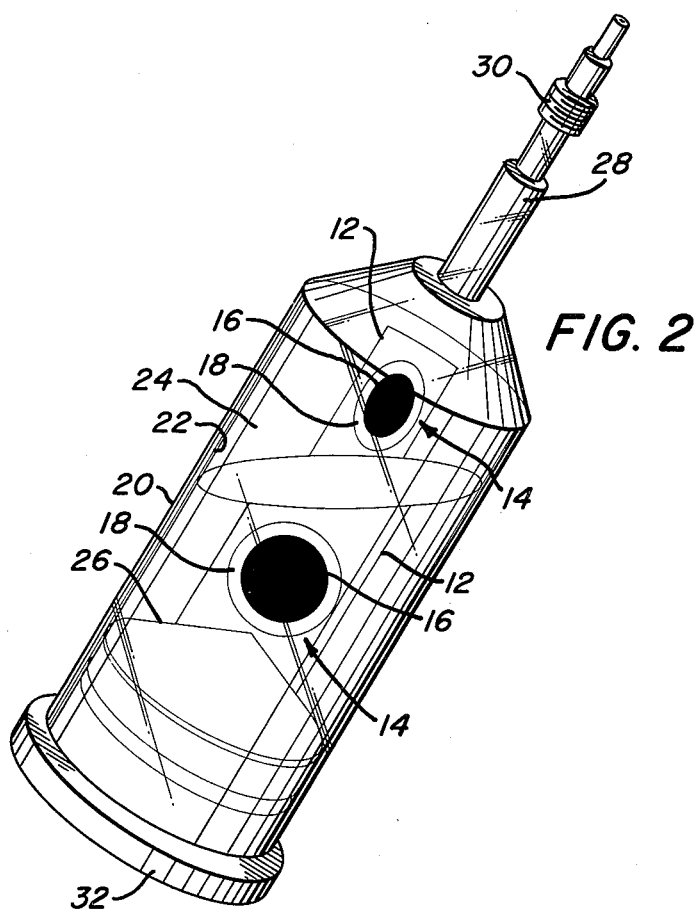
FIG. 2 is a syringe barrel and plunger assembly with a transparent liquid within the barrel illustrating he use and operation of the indicating means of the present invention.

FIG. 2 illustrates the positioning of the indicating means 10 of the present invention in conjunction with pressure jacket 20 which surrounds a syringe 22 of the type used in connection with the angiographic apparatus shown and described in U.S. Pat. No. 4,006,736. The syringe barrel is shown at 24, and the associated plunger at 26. At the forward end of the barrel 24 is a tip 28 which extends through the forward end of the pressure jacket 20. The tip 28 is threaded at 30 for connection to an appropriate catheter. At the rear portion of the syringe barrel 24 is a flange 32 which serves as an abutment face for associating with the rear portion of the pressure jacket 20.

Strip 12 is typically positioned on the back side of the pressure jacket 20 so that the indicator patterns are pressed against the pressure jacket surface and are visible through the pressure jacket and the syringe barrel. For purposes of illustration, the upper portion of the syringe barrel 24 of FIG. 2 is shown with no liquid present, and thus indicator pattern 14 is seen in its undistorted, elliptical form and is surrounded by light border 18.

The lower portion of the syringe barrel 24 contains liquid and the indicator markings in that portion appear as circles, with the transverse axis of the ellipse appearing to be as long as the longitudinal axis thereof. It should be understood that in normal use in an angiographic apparatus, the syringe will typically be either completely empty or completely full, and the present invention serves to avoid the injection into a patient of air from an empty syringe. The partially filled syringe shown in FIG. 2 illustrates the effect of the presence of liquid upon the indicator pattern as it would appear to an observer.

Figure 3:
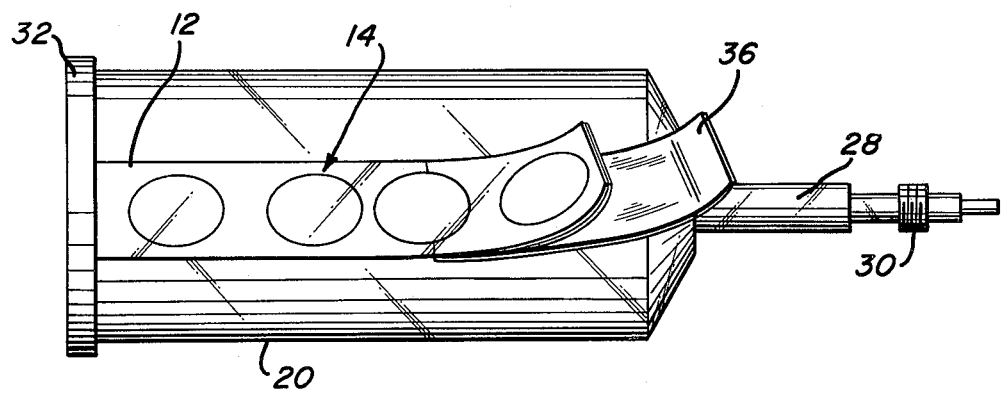
FIG. 3 is a side view of the back of the syringe barrel of FIG. 2 and illustrates one method of application of the indicating means of the present invention to the syringe barrel.

FIG. 3 illustrates a method of installation of indicating strip 10 on a syringe barrel. In order to install the device, the backing strip 36 is partially removed from the face of the indicator strip 10, an end of the strip is aligned with the flange 32 of the pressure jacket 20, and the backing strip is withdrawn allowing the adhesive surface to contact the barrel and to attach the indicator strip thereto.

The indicator strip is placed on the syringe in such a manner that it is readily viewed when the syringe is in operating position. In particular, the indicator patterns 14 are positioned along the strip 10 so that they will not all be obscured by the plunger 25 when the syringe contains the liquid material. A normal load is based upon the size of the media bottle, typically 25 or 50 ml. Spacing of the indicator patterns 14 is measured from the end of the strip 10 which will abut flange 32 when installed on the pressure jacket. By measuring from each of the ends, a single strip can be produced which is adaptable for use on two different sized pressure jackets. Proper installation then requires only that the end of clear strip 10 from which measurements for the given pressure jacket were made be placed in abutment with flange 32. In a preferred embodiment four indicator patterns are present on a strip designed for use with two syringes.

Although FIG. 2 illustrates an embodiment of the invention where indicating means 10 is a separate strip 12, it can also be applied by other means, such as direct printing by silk screening, hot stamping, or the like. Such hot stamping or silk screening will provide a more permanent, non-removable indicator pattern than the adhesively attached printed strip. However, the separate strip is useful for retrofitting existing units not having such indicating means. A preferred material for pressure jacket 20 is a polycarbonate because inks are readily available which will adhere to the material and, thus, the indicia can be readily printed on the outside or the inside of the pressure jacket 20.

To be readily able to distinguish between the presence or absence of liquid, it is preferred that the ellipses 16 be solid black and that they appear surrounded by a white border. However, depending upon the light level and type of lighting in which the indicating means is to be employed, fluorescent or other colors may be employed.

Although the foregoing description sets forth the preferred configuration for the indicating patterns forming a part of the present invention, other configurations can also be employed, if desired. However, it is preferred that there be some contrasting colors defining the pattern to facilitate viewing. While a dark central pattern with a lighter, peripheral border has been disclosed, it would be apparent that the central pattern can be a light color surrounded by a dark border, if desired.

It should be appreciated that the above description is given for purposes of illustration only, and it is not intended to limit the scope of the present invention, which is limited only as defined in the following claims.

What is claimed is:

1. In an angiographic syringe having a transparent, hollow cylindrical barrel for receiving a transparent liquid, and a plunger axially reciprocable within the barrel for discharging the liquid therefrom, the improvement comprising indicating means carried by said barrel to indicate the presence of a transparent liquid within said barrel, said indicating means including a plurality of discrete, opaque patterns of predetermined shape substantially axially disposed along said barrel, whereby the liquid alters the perceived configuration of said patterns when viewed through said barrel to provide a direct visual indication of the presence of a transparent liquid within said barrel.

2. The indicating means of claim 1 wherein said opaque patterns are provided in a dark color and include peripheral opaque areas of a contrasting, lighter color.

3. The indicating means of claim 1 wherein said opaque patterns are provided in a light color and include peripheral opaque areas of a contrasting, darker color.

4. The indicating means of claim 2 wherein said indicating means is imprinted on the outer surface of said barrel.

5. The indicating means of claim 2 wherein said indicating means is imprinted on a strip of flexible material which is adhesively secured to the outer surface of said barrel.

6. The indicating means of claim 5 wherein said patterns are axially elongated in the direction of the axis of said barrel.

7. The indicating means of claim 6 wherein said patterns are substantially elliptical and have their major axes aligned with the axis of said barrel.

8. The indicating means of claim 7 wherein said elliptical patterns are of such a configuration relative to lhe size of said barrel that the presence of liquid therewithin distorts said patterns so that they appear to be circular.

* * * * *